United States Patent [19]

Chacornac

[11] 4,109,655
[45] Aug. 29, 1978

[54] MULTI-PENETRATION VACCINATION APPARATUS

[75] Inventor: Georges Chacornac, Saint-Etienne-Loire, France

[73] Assignees: Manufacture Francaise d'Armes et Cycles de Saint-Etienne Manufrance, Saint-Etienne-Loire; Institut Pasteur, Paris-Seine, both of France

[21] Appl. No.: 732,643

[22] Filed: Oct. 15, 1976

[30] Foreign Application Priority Data

Oct. 16, 1975 [FR] France .............................. 75 32385
Nov. 10, 1975 [FR] France .............................. 75 35241

[51] Int. Cl.² ........................................... A61B 17/20
[52] U.S. Cl. ................................................. 128/253
[58] Field of Search ............................... 128/253, 173

[56] References Cited

U.S. PATENT DOCUMENTS

| | | | |
|---|---|---|---|
| 3,221,739 | 12/1965 | Rosenthal | 128/253 |
| 3,221,740 | 12/1965 | Rosenthal | 128/253 |
| 3,322,121 | 5/1967 | Banker | 128/253 |

Primary Examiner—John D. Yasko
Attorney, Agent, or Firm—Haseltine, Lake & Waters

[57] ABSTRACT

A multi-penetration vaccination apparatus comprising a mounting having on one side a manually engageable portion for the handling of the apparatus and on the other side one or more levels of supports adapted for removable press-fit of one extremity of concentric sleeves, the free extremity of the sleeves and the central support having a plurality of points for penetration into the skin of the subject. Vaccine is supplied to the points so as to penetrate into the skin along with such points. The vaccine can be contained in a reservoir formed at the bottom of a cover which is mounted on the outermost of the sleeves to form a sealed enclosure for such vaccine, the points being immersed in the vaccine. Alternatively, the central support can be formed with a bore in which a vaccine capsule is inserted so as to supply vaccine to the points at the time of penetration thereof into the skin of the subject.

30 Claims, 36 Drawing Figures

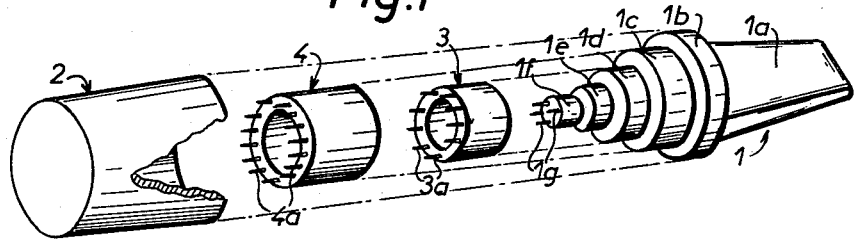
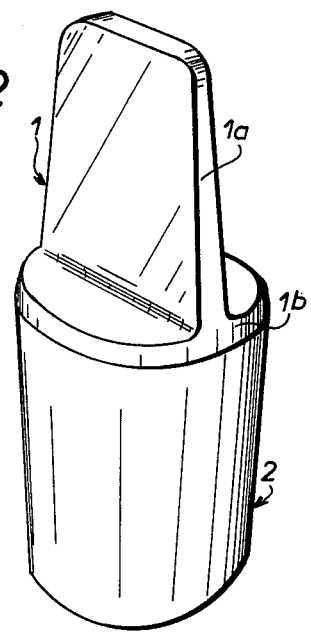
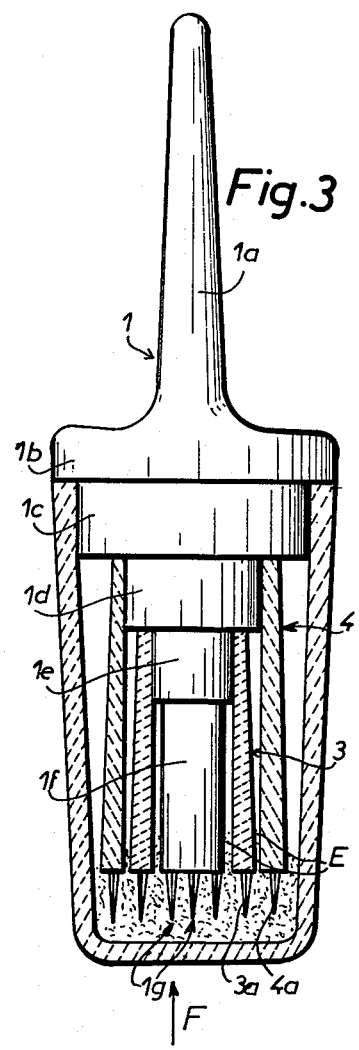
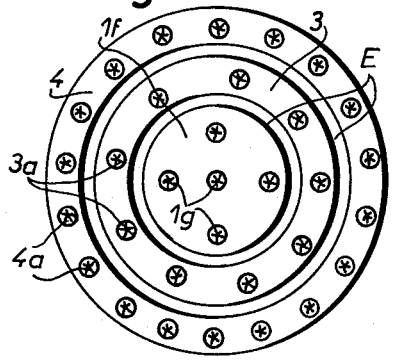

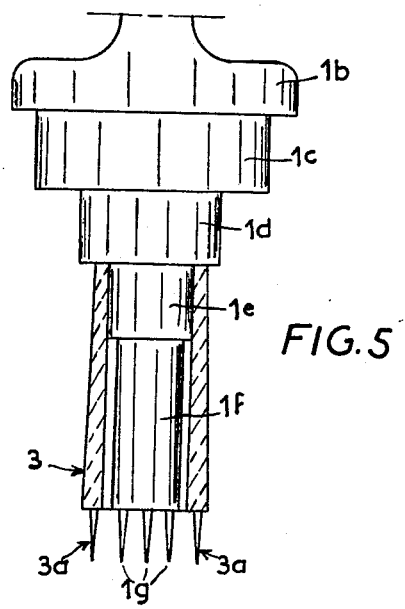
FIG.5
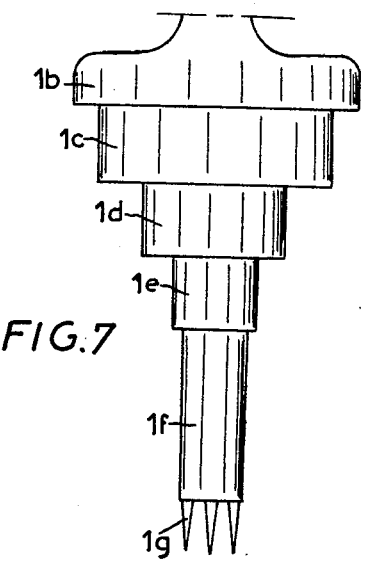
FIG.7
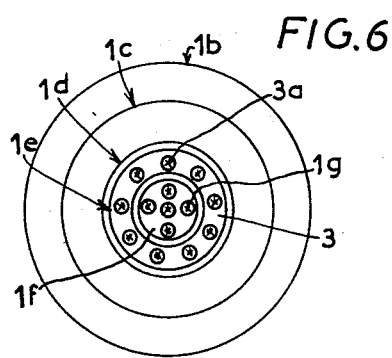
FIG.6
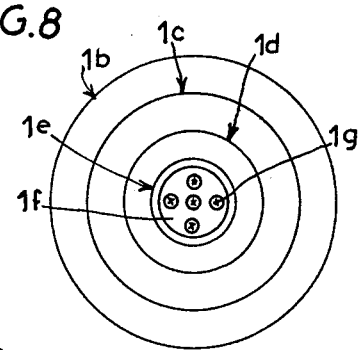
FIG.8
FIG.9
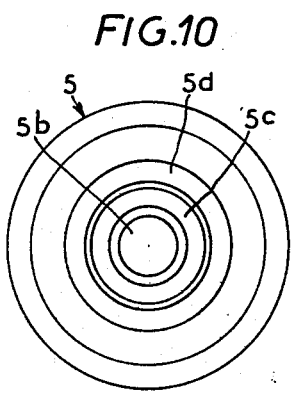
FIG.10
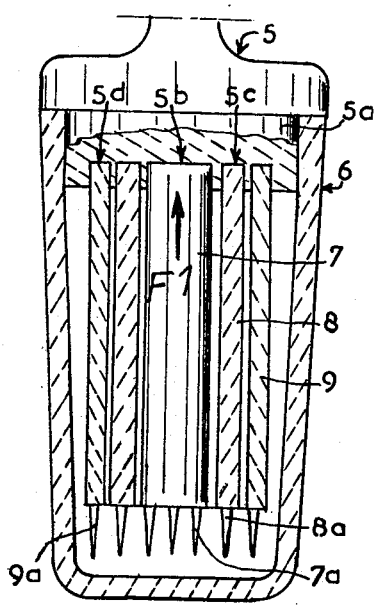
FIG.11

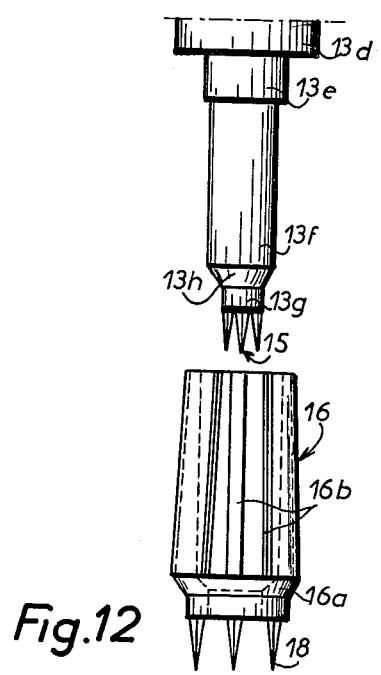
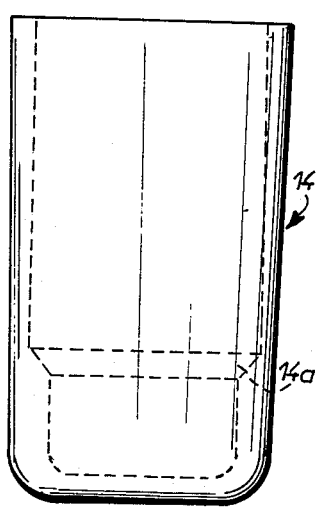
Fig.12
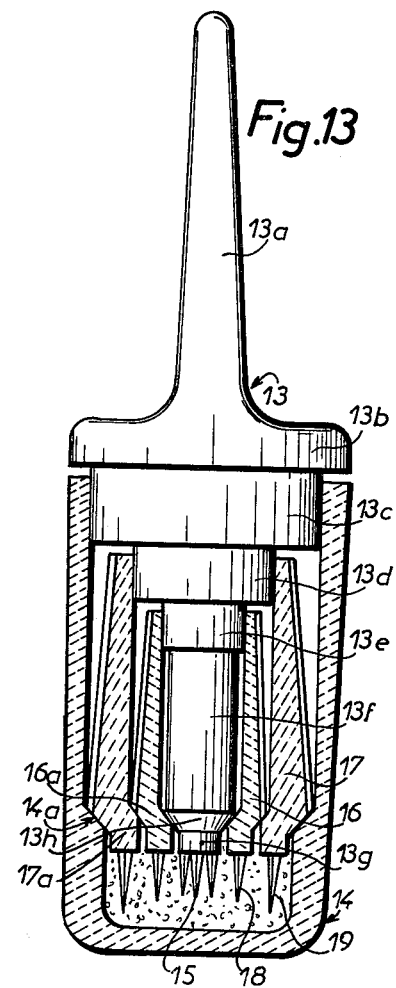
Fig.13

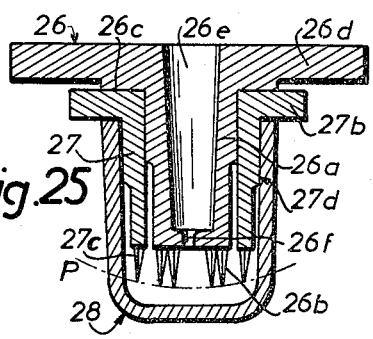
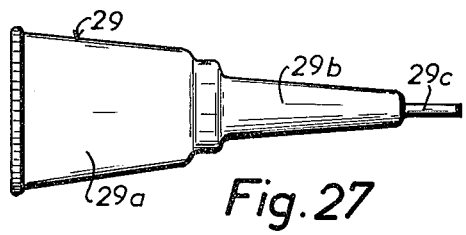
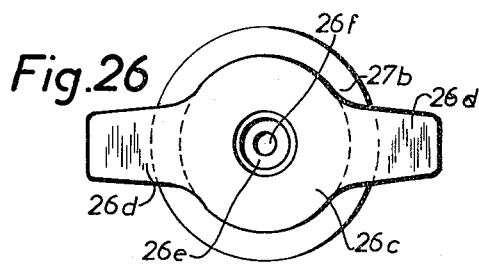
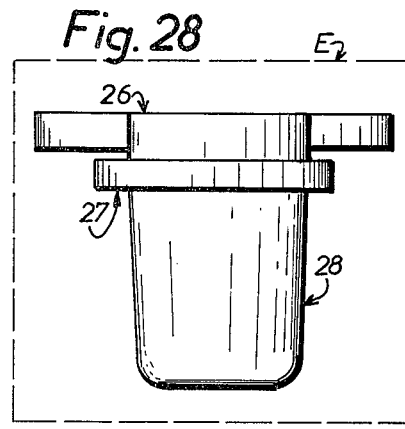
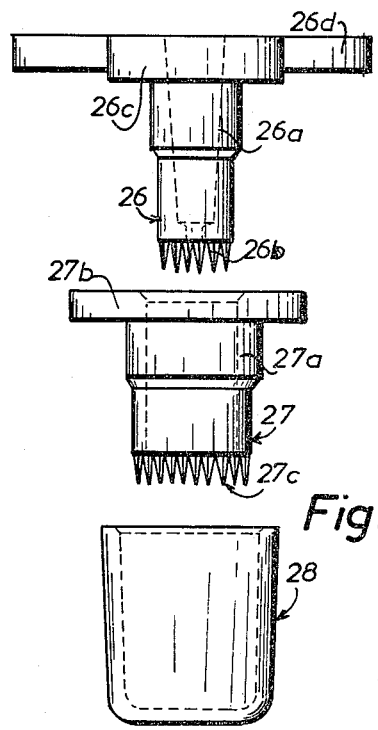
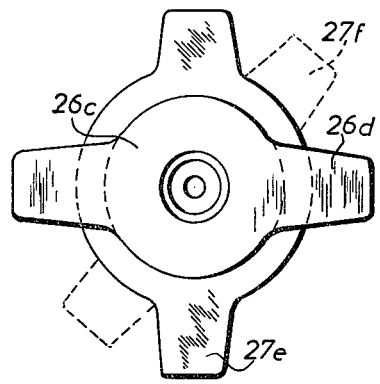

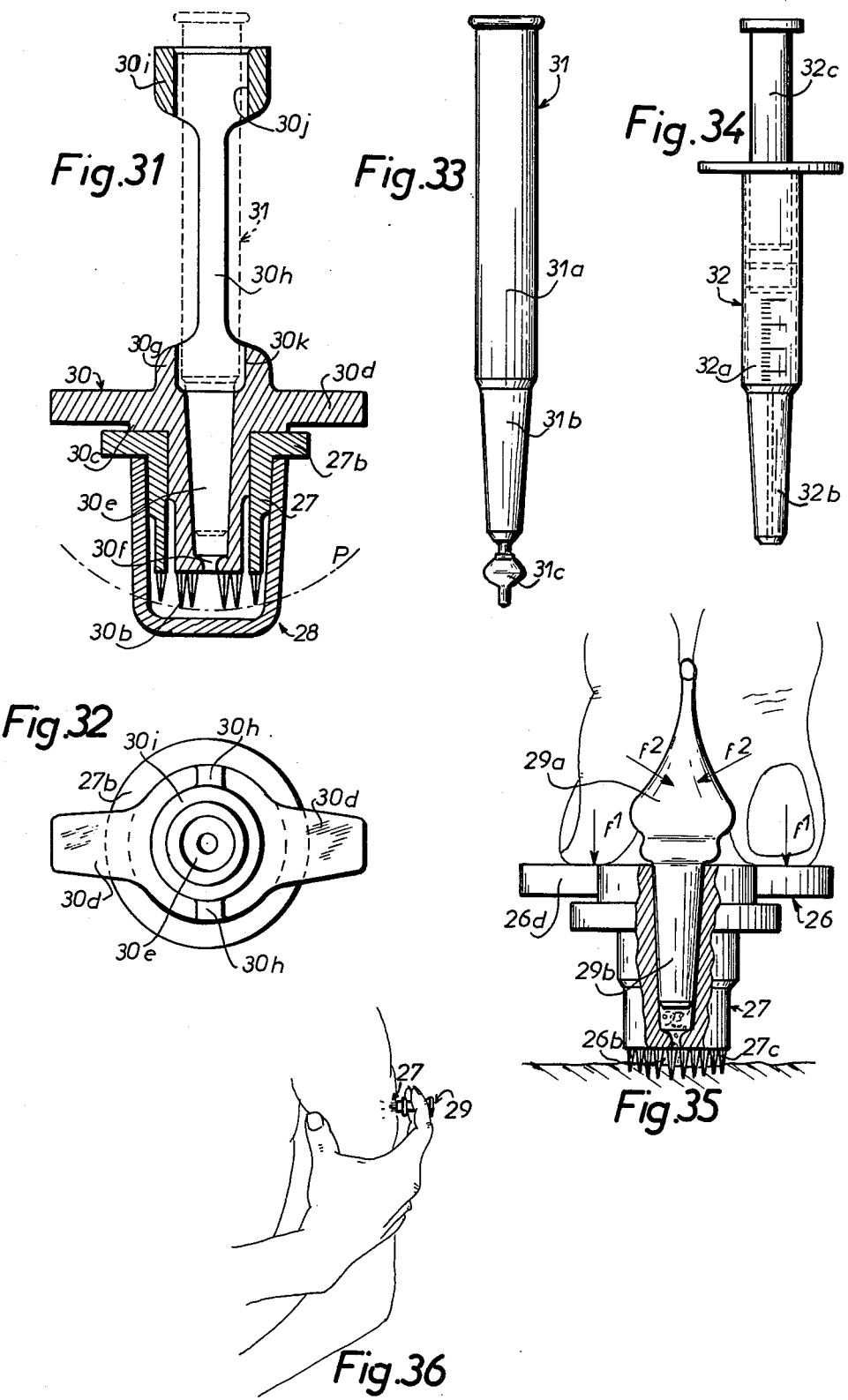

MULTI-PENETRATION VACCINATION APPARATUS

FIELD OF THE INVENTION

The invention relates to a multi-penetration vaccination apparatus having adjustable effect according to the subject to be vaccinated.

The invention relates generally to the technical field of apparatus for the introduction of agents such as vaccine into the body.

There is proposed apparatus or vaccination means having multiple points or teeth which are immersed in the vaccine to be innoculated into the vaccinated subject.

BACKGROUND

It is known that therapeutic innoculation is in direct relation to the age of the vaccinated subject. The greater the age of the subject the greater the quantity of innoculated vaccine. Generally, this leads to a number of injections in different portions of the skin of the points or teeth of the vaccination member. The effect is objectionable, if not, harmful to the vaccinated subject who can retain scars for a relatively long time. The process is difficult for the operator and leads to a loss of time.

SUMMARY OF THE INVENTION

According to the invention, these disadvantages are avoided by the provision of a multi-penetration vaccination apparatus having adjustable effect as a function of the vaccinated subjects and operative by a single pressure through the skin. The apparatus is characterized in that it comprises a mounting having on one side a manually engageable portion adapted for applying pulling and pushing forces while on the other side of this mounting there are formed one or more levels of supports or equivalent apparatus adapted for removable mounting of one extremity of concentric sleeves or of hollow members engaged with one another, the free extremity of the sleeves and of the central support having a plurality of points, teeth or other means of penetration into the skin.

According to another embodiment, the sleeves or hollow members, engaged on the supports or in concentric grooves or equivalent means, the central support which can be integral with the mounting and an optional hood or cover (when utilized), have shoulders or enlarged portions, preferably, but non-limitively, with conical contact surfaces engaging one another in a manner to retain in sealed fashion the vaccine in the portion of the hood or of the point carriers, in the zone of the points for improving the diametral rigidity of the supports and sleeves while facilitating the handling in the course of the various manipulations.

According to another important characteristic, the points or penetration means have a section in profile with a plurality of radial branches.

Another characteristic feature is that the section in profile of the branches is cruciform.

According to another characteristic feature, between the branches whose top is preferably a sharp point for pentration, there are provided angles, or internal cavities for retention of vaccine.

According to another embodiment, the mounting has integrally formed therewith a central support whose free extremity carries, at least one, and generally, a plurality of points, at least one sleeve being disposed around this carrier and being retained in removable manner by frictional engagement or by a screw, said at least one sleeve having points at its free extremity; the central support of the mounting being axially open from one end to the other in order to receive a member containing vaccine that is to be placed on the skin of the subject to be vaccinated before or at the same time that, by pressure, the points perforate the skin and innoculate the vaccine.

BRIEF DESCRIPTION OF THE DRAWING

FIG. 1 is an exploded perspective view of the elements of the vaccination apparatus according to the invention.

FIG. 2 is a perspective view on greater scale of the assembled apparatus.

FIG. 3 is a sectional view of the apparatus.

FIG. 4 is a view in the direction of arrow F in FIG. 3 showing only the penetration points positioned on their supports.

FIG. 5 is an elevational view partly in section views showing the apparatus with projection of two series of points.

FIG. 6 is a bottom plan view of the apparatus in FIG. 5.

FIGS. 7 and 8 are respectively an elevational view and a bottom plan view showing the apparatus with projection of one series of points.

FIG. 9 is a sectional view of the apparatus according to another embodiment.

FIG. 10 is a view taken in the direction of arrow F1 in FIG. 9 showing only the support for the point-carrier elements.

FIG. 11 is a partial sectional view showing the disposition of the points according to another embodiment.

FIG. 12 is a view showing the separate elements composing the apparatus according to a modified embodiment.

FIG. 13 is a sectional view showing the apparatus in FIG. 12 in assembled condition.

FIG. 25 is a sectional view of a further embodiment of the apparatus.

FIG. 26 is a plan view of the embodiment in FIG. 25.

FIG. 27 is a view showing a first embodiment of a member containing vaccine.

FIG. 28 illustrates the vaccination apparatus placed in a conditioning container.

FIG. 29 is a view showing the separate elements composing the vaccination apparatus according to FIG. 25.

FIG. 30 is a plan view showing handling means for removable sleeves.

FIG. 31 is a sectional view showing another embodiment of the vaccination apparatus.

FIG. 32 is a plan view of FIG. 31.

FIG. 33 illustrates a variation of the member containing the vaccine, more particularly adapted to the vaccination apparatus according to FIG. 31.

FIG. 34 shows a vaccine reservoir in the form of a syringe for innoculation in succession or modulated case by case.

FIGS. 35 and 36 show two examples of the operation of a vaccination apparatus with its member containing the vaccine.

DETAILED DESCRIPTION

Figure 14:
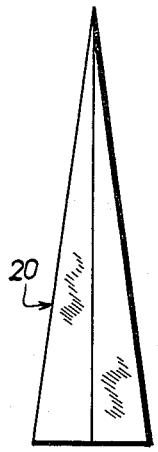
FIGS. 14 to 24 illustrate different forms of teeth or penetration points.

The apparatus according to FIGS. 1 to 8 is composed of a mounting 1 consisting of a handle portion 1a forming a palette connected to a plate 1b which is, for example, circular. The plate 1b in opposition to the palette has a plurality of support surfaces at different levels, for example, cylindrical supports 1c, 1d, 1e, 1f.

The first support 1b is adapted to receive with pressure and in sealed manner the open extremity of a protection hood or cover 2 forming at its closed lower portion a reservoir for the vaccine to be innoculated. It is to be noted that the hood is conical to facilitate its handling. Instead of a hood, a cloth cover can be provided, the vaccine being in an independent receptacle.

The last support 1f has, on its end face, points, teeth or pins 1d in determined number, for example, five (FIG. 4).

The intermediate supports 1d, 1e can be in any number (1, 2, 3 . . . ) and are intended to receive, by press fit, hollow elements such as sleeves 3, 4 . . . which when abutted at their upper shoulders against the supports are in the same alignment as their free extremity which also carries points, teeth or narrow pins 3a, 4a, . . . in determined number, for example, nine on sleeve 3 and eihteen on sleeve 4 (FIG. 4).

These sleeves have a cylindrical bore and are conical at their periphery with the larger diameter nearest to the points. This disposition permits, in combination with the dimensioning of the supports, the formation at the lower end of a small space E between the sleeves and between the sleeve 3 and the support 1f, which space is utilized to retain a certain quantity of vaccine. Furthermore, the conicity or counterslope of the sleeves facilitates their handling for engaging them or disengaging them from their supports since the thinnest wall is at the end of the sleeve which cooperates with the support.

As seen in FIGS. 5 to 8, one can thus rapidly vary and accommodate the number of points of penetration as a function of the vaccinated subject by mounting one sleeve (FIGS. 5 and 6), two sleeves (FIGS. 7 and 8) or more sleeves as desired.

The complete apparatus, that is to say with all of the points, permits the maximum desired vaccination with a single pressure against the skin. If one wishes to innoculate less vaccine, one removes one or more sleeves. For a minimum vaccination, the end support 1f alone is sufficient.

Thus, the sleeves and supports are circular for reasons of simplicity of manufacture and of concentration of the points in order to obtain a maximum innoculation on a minimum surface of skin. However, it is simple to provide other shapes leading to any concentration of supports and sleeves such as polygonal form in section (square, hexagonal).

According to a variation illustrated in FIGS. 9 and 10, the mounting 5 has a single support 5a adapted to receive the hood 6 and in the end face of the support are formed an axial bore or recess 5b in which is forceably engaged a smooth support 7 having teeth 7e and concentrical circular grooves 5c, 5d receiving sleeves 8, 9 having teeth 8a, 9a.

One can also integrally form a central support with the body in place of the support 7.

It is to be further noted that the teeth or points can be of the same length or of different lengths as shown in FIG. 11 where it is seen that short teeth 10 are at the center and longer teeth 11 at the periphery, the teeth 12 being of intermediate length. In order to obtain the same effect, one can provide points of the same length, but sleeves of different lengths (in the case of FIG. 9), or sleeves whose free ends are not at be same level (in the case of FIG. 3).

This different penetration of the points permits adaptation of the depth of innoculation to the particular subject.

For example, and non-limitatively, the following dimensions can be given:

length of the assembled apparatus: about 39 mm exterior diameter or circumscribed diameter: about 12 mm length of the palette: about 17 mm length of the points: about 3 mm; or 2.5, 2.8 or 3 mm, if they are of different lengths conicity of the sleeves 2: about 2° space between the sleeves: about 0.5 mm

According to these dispositions, the following is especially noted:

rapid adaptation to the vaccinated subject of the quantity of vaccine to be innoculated by the removability of the elements carrying the points, thus assuring a precise vaccination as a function of the subject, notably as a function of his age. This is effected by application of pressure, once, against the skin;

the concentration of the innoculation points by the arrangement of the points permits a maximum innoculation on a minimum skin surface and avoids more substantial scarring; and the spaces between the sleeves assures the retention of the vaccine.

In FIGS. 12 and 13, there is shown a variation of the vaccination apparatus whose mounting permits removable engagement of the sleeves or hollow elements on the staged cylindrical supports of the mounting, and it is obvious that these sleeves can be mounted by utilizing dispositions equivalent to those of the concentric grooves described previously.

The mounting 13 has, as in the first embodiment, a handling portion 13a forming a palette connected to a plate 13b of circular or other section. Opposed to the palette, the plate is prolonged by successive cylindrical supports 13c, 13d, 13e, 13f, 13g. The first cylindrical support 13c receives, with pressure fit, the open end of a cover or hood 14 whose base contains the vaccine to be innoculated.

The last support 13g has, on its end face, means for penetration of the skin (for example, teeth or points 15) in suitably determined number.

The intermediate supports 13d, 13e can be present in any number and receive by force fit sleeves or hollow elements 16, 17 carrying at their extremities penetration means (teeth or points 18, 19) in any suitably determined number.

The sleeves 16, 17 preferably have enlarged portions or shoulders 16a, 17a near their extremity carrying the points with conical contact surfaces. The same conical disposition is found in the form of shoulder or chamfer 13h between supports 13f and 13g and at the interior of the hood 14 (surface or chamfer 14a). In the framework of the invention, the enlarged portions or shoulders can have contact surfaces extending perpendicular to the general axis of the apparatus.

These contact surfaces assure an efficient sealing of the mounting to avoid ascension of the vaccine along the length of the sleeves in the course of handling. In effect, the sleeve 16 force fit on the support 13e, bears against the surface 13h and against sleeve 17, the latter being force fit on support 13d, and bearing against shoulder 16a of the sleeve 16 and against the hood 14 which is force fit on the support 13c.

It is to be noted further that in order to facilitate the force fit and the disengagement of the sleeves, discontinuities are provided on the periphery of the sleeves, such as channels 16b, 17b, striations, grooves, knurling. In a manner to improve the preceeding embodiment, a more substantial conicity of the sleeves is provided to augment the rigidity and facilitate the handling and manipulation.

The points for penetration in the skin are preferably in the form of teeth or narrow pins. There are shown in FIGS. 14–24 different shapes of the points or teeth which can be of equal or unequal length.

Figure 15:
Figure 21:
Figure 22:

For example, in FIGS. 15, 21 and 22, there are seen points which in section have three or four branches with planar, convex or concave connecting surfaces.

Figure 16:
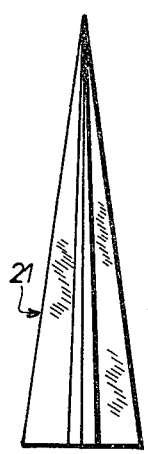
Figure 18:
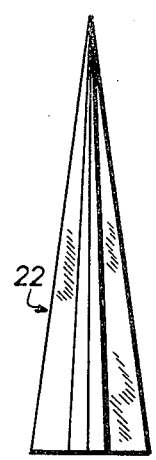
Figure 20:
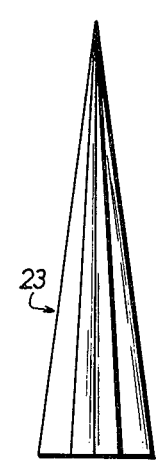
Figure 17:
Figure 19:

In FIGS. 16 and 17, the points 21 are of cruciform section with narrow branches; in FIGS. 18 and 19 the points 22 are of cruciform section with thick branches and in FIGS. 20 and 21 the points 23 have a cruciform section with thick branches and curved faces (concave or convex).

In FIG. 22, the points 25 have a polygon section with concave surfaces.

In its various forms, the surfaces between the edges of the branches constitute vaccine reservoirs.

Figure 23:
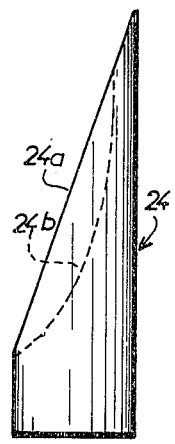
Figure 24:
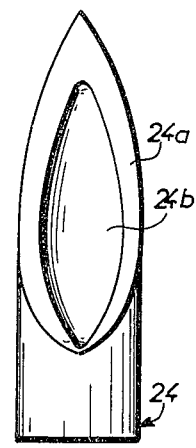

Finally, in FIGS. 23 and 24 there is illustrated the conformation of a variation comprising a cylindrical point 24 with beveled edge 24a and having one or more cavities or concave recesses 24b.

According to this embodiment, it is noted in particular that:

the sealability of the apparatus at the level of the shoulders and of the contact faces 13h, 16a, 17a, 14a prevents the vaccine from flowing and disposing itself ineffectively along the length of the sleeves;

the shoulders or the enlargements of the sleeves augment the rigidity, notably the diametral or transverse rigidity. The mounting of each sleeve serves to complete the mounting of the preceedingly engaged sleeve and consequently the sealing of the assembly. The disposition of the shoulders or enlargements has the effect of thus enlarging the handling portion relative to the points to minimize the possibility of contact of the fingers with the vaccine and the points;

the use of teeth or points of different lengths, in which the smallest length is preferably at the center, assures a progressive and easier penetration under a reduced pressure while eliminating or minimizing discomfort to the patient;

the sectional profiles with a plurality of radial branches, cruciform, beveled, faceted or with cavities or chambers permits better retention of the vaccine between the branches or in the internal cavities, notably by the effect of surface tension. These points or pins, for a surface or section of equivalent penetration, have a much greater carrier surface which permits reduction of the number of points without recourse to the capillarity effect by extreme reduction of the points;

better penetration of the vaccine by the effect of the radial branches of the points, which open the skin in a corresponding manner without the lips of the skin compressing or wiping the vaccine dry, and, particularly, the vaccine disposed in the angles or internal cavities between the branches.

In FIGS. 25, 26, 28, 29, 35 and 36, there is seen a vaccination apparatus according to another embodiment in which the apparatus comprises a mounting 26 constituted of a central cylindrical carrier 26a having two support levels and whose free extremity carries at least one and generally a plurality of penetration points 26b.

At the upper portion of the mounting is a cylindrical shoulder 26c partially extended, for example, with diametrically opposed lugs 26d.

Axially, the mounting has a conical bore 26e terminating at the narrowest portion in a throttle opening 26f which has a free open extremity.

On a first support surface 26a, the bore 27a of a sleeve 27 is frictionally engaged, the sleeve 27 having an upper collar 27b bearing against shoulder 26c of the mounting and points 27c at the free annular extremity.

One or more additional sleeves can be frictionally engaged on the exterior diameter of the first sleeve 27. In the embodiment illustrated there is only one single sleeve. The exterior diameter 27d of the sleeve 27 frictionally receives a hood 28 intended to protect the points from a mechanical point of view (to avoid damage by shock or impact) and from a medical point of view (to assure the sterilization), it being understood that this sterilization is also realized at the upper open portion at 26e by mounting the apparatus in a packing E (FIG. 28).

It is to be noted that the points 26b and 27c are of different lengths in order that the points 26b closest to the axis of the mounting will be the longest and the points situated at the greatest diameter will be ths shortest, and together constitute an imaginary surface P (FIG. 25) which is convex with respect to the axis in the direction of penetration of the points.

In FIG. 27 there is illustrated a member adapted to contain the vaccine to be innoculated according to a first embodiment constituted by a flexible capsule 29 comprising a reservoir portion 29a followed by a conical end 29b adapted to be mounted in the bore 26e of the mounting and a breakable tip 29 c.

The end 29b and the bore 26e have a suitable conicity and, for example, conform to French standard S90011.

According to another embodiment illustrated in FIGS. 31 and 32, the vaccination apparatus has one or more sleeves 27 and a hood 28 whereas the mounting 30 has a central support 30a with the points 30b, cylindrical portion 30c, lugs 30d and conical bore 30e with lower throttle outlet 30f.

The upper portion of the portion 30c has a boss 30g prolonged vertically by at least two ribs 30h connected at the upper portion to a ring or bearing 30i. The ribs are situated outside a diameter limited by a bore 30j of bearing 30i and by a reamed portion 30k on the boss 30g opening into the conical groove 30e.

This particular embodiment of the mounting permits the engagement and guiding of a vaccine container (FIG. 33) having the shape of a flexible tube 31 comprising a reservoir portion 31a followed by a conical end 31b corresponding to the bore 30e of the mounting and a breakable tip 31c.

In FIG. 34 there is shown another embodiment of vaccine container 32 of the syringe type comprising a reservoir body 32a terminated by a conical end 32b corresponding to the conical bore of the mounting and a piston 32c.

This arrangement permits a controlled distribution and dosing, as desired, of the vaccine, case by case, by the practitioner.

It is to be noted that the flexible tube 31 and the syringe 32 can be also utilized with the vaccination apparatus according to the previous embodiment.

There is further shown a particular disposition to facilitate the handling, notably, the lugs 26d or 30d permitting the easy separation of the removable sleeve 27 whose upper collars 27b extend beyond the cylindrical portion 26c or 30c of the mounting (FIGS. 26 and 32). The sleeve can also be provided with additional lugs 27e, 27f (FIG. 30) spaced angularly with respect to the lugs 26d of the mounting.

According to another embodiment, the mounting and the sleeves can be of different color in order to facilitate the manipulations. This differentiation of color can be realized on the elements in entirety or only on the lugs or collars.

Next will be described the manner of operating the vaccination apparatus with reference to FIGS. 31, 35 and 36 of the drawings.

In FIG. 35, there is seen a complete vaccination apparatus, namely, comprising a maximum number of penetration points in which there is frictionally engaged a vaccine capsule 29. The practitioner holds the capsule between the thumb and the index finger and presses the vaccinator against the skin of the patient while bearing on the faces of the capsule (arrows f1, f2); the extremity of the pressing fingers being in contact with the lugs of the mounting. The vaccine thus flows through the opening 26f into the space between the points and a certain quantity penetrates into the epidermis.

According to another manner of use, the practitioner holds the capsule engaged with friction in the bore 26e between the index finger and the next finger to compress the capsule and bears against the lugs of the mounting (FIG. 36 where the mounting is seen in operation) whereas the thumb is held behind the arm to form a counter-bearing force in reaction to the pressure force.

With the flexible tube 31 the action is similar in the sense that the practitioner holds the tube engaged with friction in the mounting and presses the apparatus against the skin while compressing the tube.

If the practitioner employs a graduated syringe 32, he takes the assembly of the syringe and vaccinator in one hand and holds it against the skin and activates the piston 32c with the other hand to deliver a measured quantity of vaccine.

In addition to the advantages resulting from the description, the following are noted in particular;

the easy manipulation of the assembly of the vaccinator-vaccine container as well as the removable elements of the vaccinator by the different colors of the lugs or the different colors of the removable elements and mounting;

precise dosage of the vaccine avoiding significant waste thereof by its introduction into the vaccinator simultaneously with penetration at the place to be distributed instead of being retained in certain places of the points, sleeves and the mounting;

the sterile condition of the vaccinator apparatus and optionally the vaccine container;

the penetration first of the central points then of the extreme points by their different lengths or the different length of the mounting and the sleeves assuring a better effect of vaccination since the vaccine is introduced in the central portion.

What is claimed is:

1. Multi-penetrating vaccination apparatus comprising manually engageable mounting means, at least one sleeve comprising means including a plurality of points for penetrating the skin of a patient, said mounting means including a projection with a plurality of points for penetrating the skin of the patient, support means on said mounting means for removable engagement of said sleeve thereon, and means for supplying vaccine to said points with the sleeve engaged on the support means for innoculation of the vaccine into a subject when said points penetrate the skin.

2. Apparatus as claimed in claim 1 wherein said support means comprises a plurality of support surfaces at different levels for respectively receiving a respective said sleeve.

3. Apparatus as claimed in claim 1 wherein a plurality of said sleeves are provided for respective mounting on the support means, said sleeves having lower ends remote from said support means, said points being on said lower ends of the sleeves.

4. Apparatus as claimed in claim 3 wherein said lower ends of the sleeves are disposed in a common plane.

5. Apparatus as claimed in claim 3 wherein said sleeves are coaxially arranged, the lower ends of the sleeves being progressively less distant from the mounting means in accordance with the radial distance of the sleeves from their common axis.

6. Apparatus as claimed in claim 3 wherein said points are of the same length.

7. Apparatus as claimed in claim 3 wherein said projection comprises a central support having a lower end with a plurality of said points thereon.

8. Apparatus as claimed in claim 7 wherein the points on said central support and said sleeves are of different length, the points on the central support being shortest and the length of the points on the sleeves increasing in accordance with the diameter of the sleeves.

9. Apparatus as claimed in claim 7 wherein said support means is constituted by a plurality of grooves each for receiving a respective said sleeve.

10. Apparatus as claimed in claim 7 wherein said sleeves have a conical outer peripheral surface.

11. Apparatus as claimed in claim 10 wherein said sleeves have varying thickness and the thinnest end of each sleeve engages said support means.

12. Apparatus as claimed in claim 7 wherein said sleeves and central support define narrow spaces therebetween for retention of vaccine.

13. Apparatus as claimed in claim 1 wherein said mounting means comprises a plate and a flat portion extending from said plate on one side thereof for manual handling, said support means being on said plate on the other side thereof remote from said flat portion.

14. Apparatus as claimed in claim 13 comprising a cover mountable on said support means for enclosing said sleeves, said cover defining a vaccine reservoir serving as the means for supplying vaccine to said points.

15. Apparatus as claimed in claim 14 wherein said central support, said sleeves and said cover have facing conical contact surfaces which form seals therebetween and seal said enclosure when the cover and sleeves are mounted on said support means.

16. Apparatus as claimed in claim 1 comprising means on said sleeve for facilitating the handling thereof for engagement and removal with said support means.

17. Apparatus as claimed in claim 1 wherein said points are each of circular section and have a beveled end to facilitate penetration in the skin and for retention of vaccine.

18. Apparatus as claimed in claim 1 wherein said points have a recess in said beveled end for retention of vaccine.

19. Apparatus as claimed in claim 1 wherein said points have a plurality of radial branches.

20. Apparatus as claimed in claim 19 wherein said branches have sharp edges and define cavities for retention of vaccine between said edges.

21. Apparatus as claimed in claim 1 wherein said points have a cruciform cross-section.

22. Apparatus as claimed in claim 1 wherein said projection comprises a central support having a lower end with at least one point thereon, said one sleeve being mountable on said support and having a lower end with at least one said point thereon, said central support having a bore, said means for supplying vaccine being mountable in said bore to supply vaccine to the skin of the patient when the points penetrate the skin by applying pressure to said mounting means.

23. Apparatus as claimed in claim 22 wherein a plurality of said points are provided on said sleeve and a plurality of said points are provided on said central support, said points having tips defining an imaginary convex surface, the longest points being in the central support.

24. Apparatus as claimed in claim 22 comprising a removable cover enclosing said central support and said sleeve and said points thereon.

25. Apparatus as claimed in claim 22 comprising lugs on said mounting means extending radially beyond said sleeve to facilitate separation of the support means and said sleeve.

26. Apparatus as claimed in claim 22 wherein said means for supplying vaccine comprises a flexible capsule including a conical portion and a removable tip, said bore in said central support being correspondingly conical to receive said conical portion of the capsule.

27. Apparatus as claimed in claim 26 comprising a plurality of upstanding projections on said mounting means flanking said capsule when the conical portion thereof is engaged in said bore and a ring on said projections encircling said capsule.

28. Apparatus as claimed in claim 22 wherein said means for supplying vaccine comprises a syringe insertable in said bore and including means for regulating the dosage of vaccine to be delivered to said points.

29. Apparatus as claimed in claim 22 comprising a sealed container having a hollow for receiving said mounting means and sleeve in sterilized sealed relation.

30. Apparatus as claimed in claim 3 wherein said sleeves are of different color, in at least a part thereof, to facilitate distinction therebetween and selective removal according to the subject to be vaccinated.

* * * * *